(12) United States Patent
Kaldany

(10) Patent No.: US 6,659,996 B1
(45) Date of Patent: Dec. 9, 2003

(54) DEVICE FOR DELIVERING BIOLOGICAL AGENTS

(75) Inventor: Antoine Kaldany, Chestnut Hill, MA (US)

(73) Assignee: InterMed, Inc., Chestnut Hill, MA (US)

( * ) Notice: Subject to any disclaimer, the term of this patent is extended or adjusted under 35 U.S.C. 154(b) by 0 days.

(21) Appl. No.: 09/405,933

(22) Filed: Sep. 27, 1999

Related U.S. Application Data

(63) Continuation-in-part of application No. 09/266,380, filed on Mar. 11, 1999, which is a continuation-in-part of application No. 08/552,467, filed on Nov. 9, 1995, now Pat. No. 5,906,599.

(51) Int. Cl.[7] .............................................. A61M 31/00
(52) U.S. Cl. .................. 604/508; 604/509; 604/164.03; 604/164.08; 604/165.02; 604/170.02; 604/103.06; 606/15
(58) Field of Search ........................... 604/60, 264, 48, 604/500, 506–509, 158–160, 164.01–164.03, 164.08, 164.11, 164.12, 165.01, 165.02, 166.01, 170.01–170.03, 98.01, 103.01–103.06; 606/13–15

(56) References Cited

U.S. PATENT DOCUMENTS

| | | |
|---|---|---|
| 387,480 A | 8/1888 | Alleman |
| 737,293 A | 8/1903 | Summerfeldt |
| 806,746 A | 12/1905 | Miller |
| 2,634,726 A | 4/1953 | Hanson |
| 2,705,949 A | 4/1955 | Silverman |
| 3,477,423 A | 11/1969 | Griffith |
| 3,606,878 A | 9/1971 | Kellogg, Jr. |
| 3,662,754 A | 5/1972 | Halloran |
| 3,995,619 A | 12/1976 | Glatzer |

(List continued on next page.)

FOREIGN PATENT DOCUMENTS

| | | |
|---|---|---|
| EP | 0207726 | 7/1987 |
| WO | 89/10091 | 11/1989 |
| WO | 91/10399 | 7/1991 |

*Primary Examiner*—Brian L. Casler
*Assistant Examiner*—Jeremy Thissell
(74) *Attorney, Agent, or Firm*—Hamilton, Brook, Smith & Reynolds, P.C.

(57) ABSTRACT

A biological agent delivery device for delivering biological agents includes a sheath having a longitudinally extending wall surrounding an interior region, and a closed tip at a distal end. A flexible pouch formed in the sheath wall for containing a biological agent is capable of being displaced radially outwardly for radially displacing the biological agent.

30 Claims, 9 Drawing Sheets

U.S. PATENT DOCUMENTS

| | | |
|---|---|---|
| 4,178,810 A | 12/1979 | Takahashi |
| 4,402,308 A | 9/1983 | Scott |
| 4,411,657 A | 10/1983 | Galindo |
| 4,461,280 A | 7/1984 | Baumgartner |
| 4,537,593 A | 8/1985 | Alchas |
| 4,578,059 A | 3/1986 | Fabricant et al. |
| 4,600,014 A | 7/1986 | Beraha |
| 4,609,370 A | 9/1986 | Morrison |
| 4,699,154 A | 10/1987 | Lindgren |
| 4,700,692 A | 10/1987 | Baumgartner |
| 4,701,164 A | 10/1987 | Cassou et al. |
| 4,702,261 A | 10/1987 | Cornell et al. |
| 4,735,611 A | 4/1988 | Anderson et al. |
| 4,776,346 A | 10/1988 | Beraha et al. |
| 4,820,267 A | 4/1989 | Harman |
| 4,842,585 A | 6/1989 | Witt |
| 4,871,094 A | 10/1989 | Gall et al. |
| 4,881,551 A | 11/1989 | Taylor |
| 4,900,303 A | 2/1990 | Lemelson |
| 4,900,304 A | 2/1990 | Fujioka et al. |
| 4,907,598 A | 3/1990 | Bauer |
| 4,913,142 A | 4/1990 | Kittrell et al. |
| 4,917,100 A | 4/1990 | Nottke |
| 4,940,061 A | 7/1990 | Terwilliger et al. |
| 4,958,625 A | 9/1990 | Bates et al. |
| 4,986,814 A | 1/1991 | Burney et al. |
| 5,049,131 A * | 9/1991 | Deuss ................. 604/98.01 |
| 5,127,419 A | 7/1992 | Kaldany |
| 5,226,426 A | 7/1993 | Yoon |
| 5,271,744 A | 12/1993 | Kramer et al. |
| 5,304,119 A | 4/1994 | Balaban et al. |
| 5,358,474 A | 10/1994 | Kaldany |
| 5,364,365 A | 11/1994 | Wortrich |
| 5,372,585 A | 12/1994 | Tiefenbrun et al. |
| 5,405,324 A | 4/1995 | Wiegerinck |
| 5,419,765 A * | 5/1995 | Weldon et al. ............... 604/507 |
| 5,562,613 A * | 10/1996 | Kaldany ................. 604/264 |
| 5,893,840 A * | 4/1999 | Hull et al. ............ 604/103.02 |
| 5,906,599 A * | 5/1999 | Kaldany ................. 604/264 |
| 6,010,480 A * | 1/2000 | Abele et al. ........... 604/103.06 |
| 6,258,070 B1 * | 7/2001 | Kaldany ................. 604/264 |

\* cited by examiner

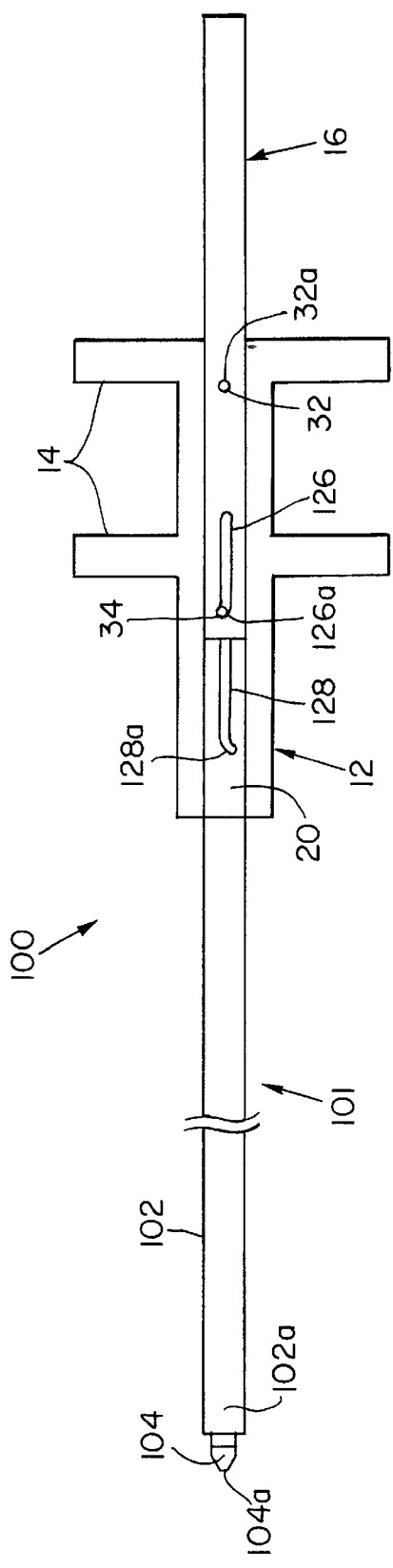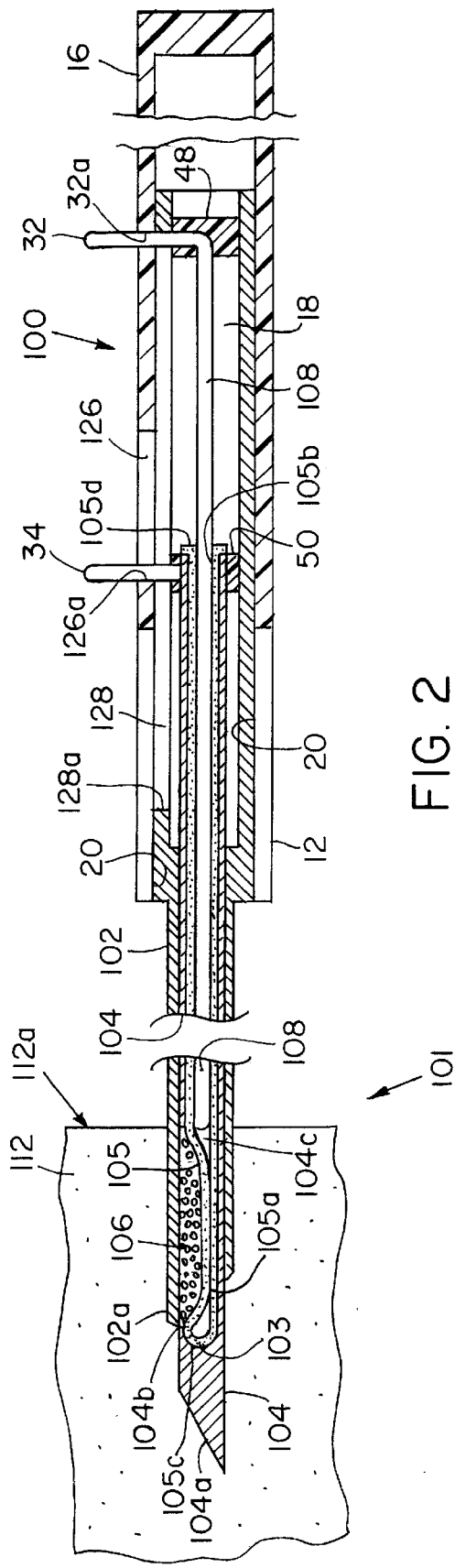
FIG. 1
FIG. 2

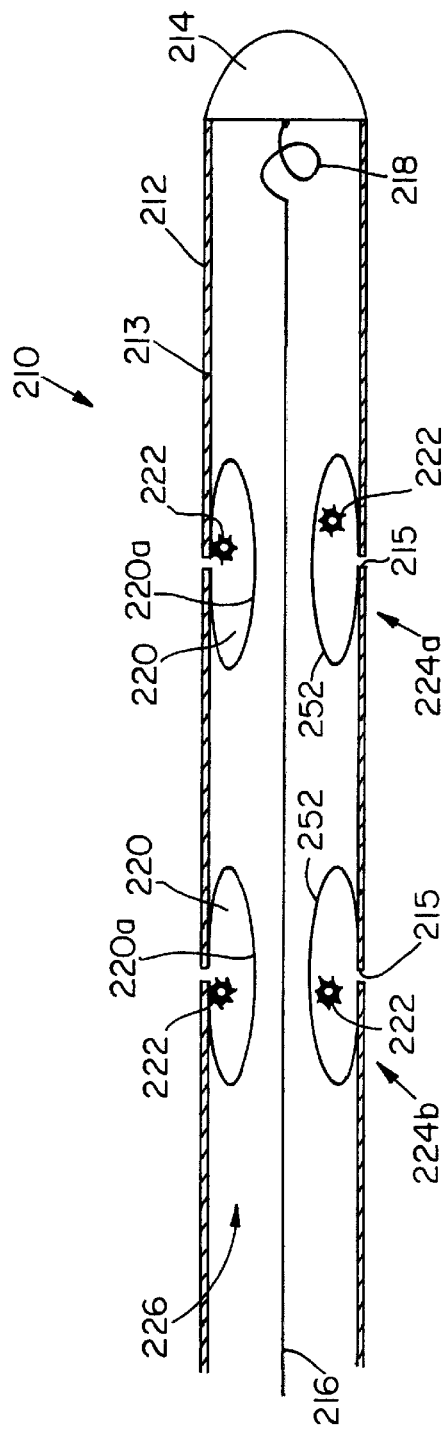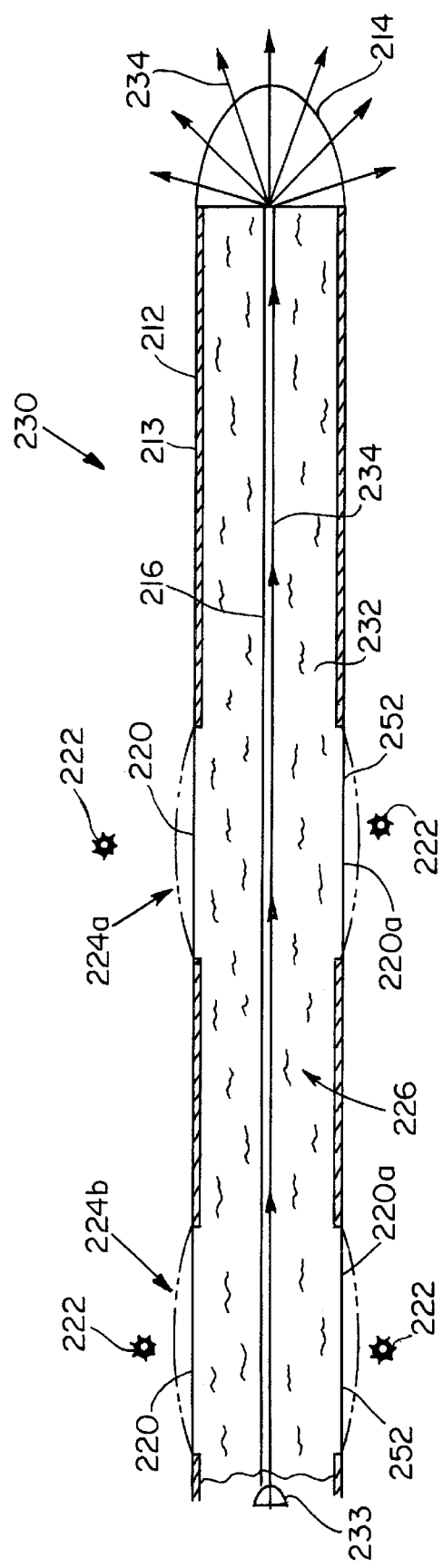

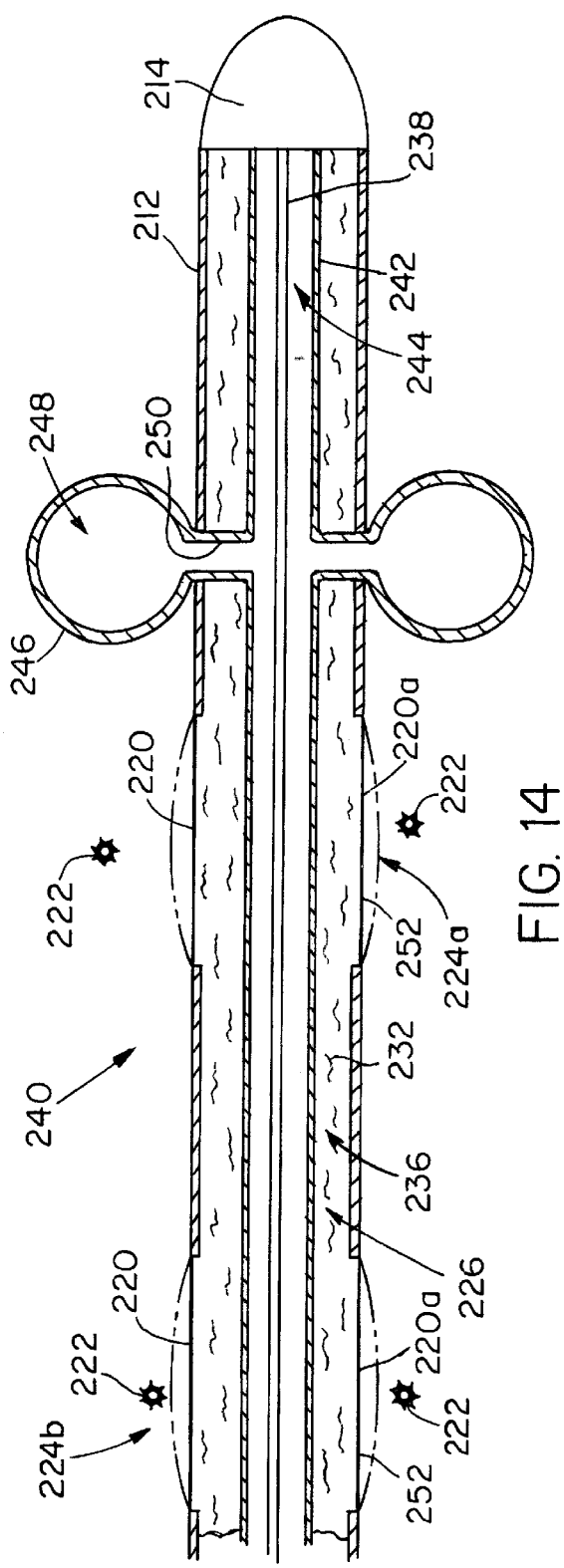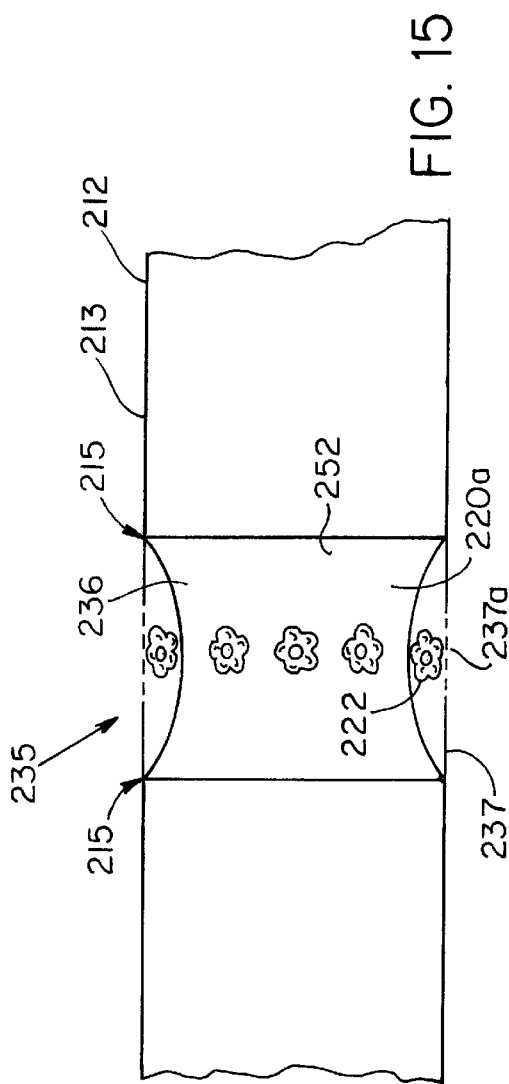

DEVICE FOR DELIVERING BIOLOGICAL AGENTS

RELATED APPLICATION

This application is a continuation-in-part application of U.S. application Ser. No. 09/266,380, filed Mar. 11, 1999, which is a continuation-in-part application of U.S. application Ser. No. 08/552,467, filed Nov. 9, 1995 now U.S. Pat. No. 5,906,599, the entire teachings of which are incorporated herein by reference.

BACKGROUND OF THE INVENTION

Much effort has been expended in recent years to find an effective and superior way of administering drugs to patients' bodies. Products such as the transdermal patch and once-a-day orally administered pills that more precisely deliver drugs have been developed. Such products are a boon to patients for they boost the effectiveness of the drugs and limit side effects by precisely controlling how quickly drugs are released in the body; by keeping drugs at a constant level and by delivering them exactly where needed.

One such development is the injection or implantation of drugs in the form of in microscopic particles or pellets at a disease site. The drugs are encapsulated in polymers or fatty compounds, such as liposomes which permit slow release of the encapsulated drug over time thereby potentially lowering the drugs toxicity.

In addition, there are times when it is desirable to deliver a biological agent that is in a non-conventional form to a disease site such as a drug in a loose particulate form, or a quantity of cells, cell clusters or cellular extracts in a bibcompatible solution. A particulate biological agent can be in a granular, powdered, or microsphere form. The problem with biological agents in these forms is that they are difficult to properly deliver to a diseased tissue site.

SUMMARY OF THE INVENTION

The present invention provides a novel device with a distal end insertable into the tissue or a body cavity of a patient for delivering both particulate and liquid biological agents in a quick, predictable, safe and easy manner without damaging the biological agent. This is important in the delivery of cells or microspheres.

The present invention is directed to a biological agent delivery device including a sheath having a longitudinally extending wall surrounding an interior region, and a closed tip at a distal end. A flexible pouch formed in the sheath wall for containing a biological agent is capable of being displaced radially or laterally outwardly for radially displacing the biological agent.

In preferred embodiments, a displacement member is disposed within the sheath for causing displacement of the pouch radially with respect to the sheath to radially or laterally deliver the biological agent. The sheath is flexible and the pouch is preformed in the sheath wall. A guide wire extends within the sheath for guiding the delivery device. Preferably, the pouch system encircles the sheath. In one preferred embodiment, the displacement member includes a spring member. In another preferred embodiment, the displacement member includes a volume of fluid. The volume of fluid can be either a liquid or a gas. Optionally, a light source is included for directing light within the sheath. The light is transmitted to the tip of the delivery device by the fluid within the sheath. In yet another embodiment, the light is transmitted to the tip of the delivery device by a fiber optic disposed within the sheath. The tip is formed in a manner to produce or deliver a desired pattern of light. In still another preferred embodiment, a balloon extends from the sheath for controlling fluid flow within body cavities.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a plan view of a preferred biological agent delivery device.

FIG. 2 is a side sectional view of the biological agent delivery device of FIG. 1 with the distal end of the device inserted into tissue.

FIG. 11 is a side schematic view of a preferred biological agent delivery catheter.

FIG. 13 is a side sectional view of another preferred biological agent delivery catheter.

FIG. 14 is a side-sectional view of still another preferred biological agent delivery catheter.

FIG. 15 is a side view of another preferred pouch arrangement.

DETAILED DESCRIPTION OF THE INVENTION

Figure 3:
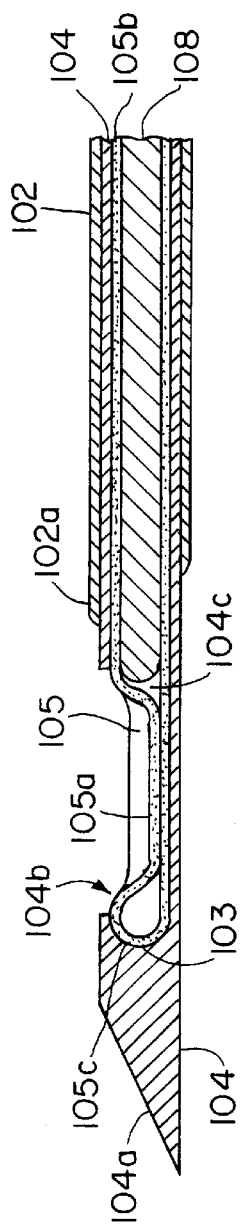
FIG. 3 is a side sectional view of the distal end of the biological agent delivery device with the outer tube 102 retracted to expose the cannula notch 104b and the support surface 105a of the flexible membrane 105.
Figure 4:
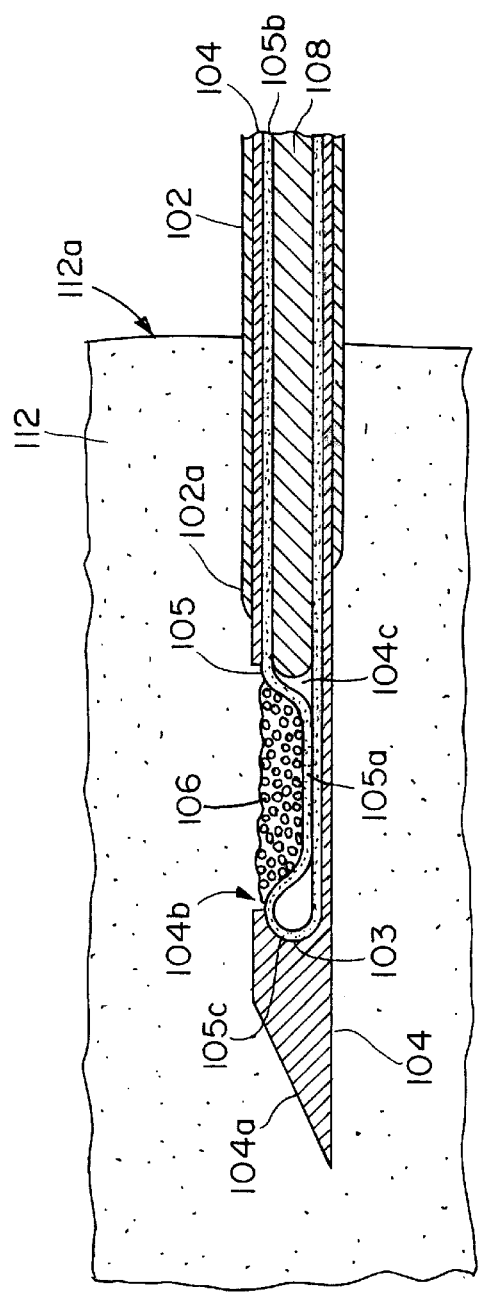
FIGS. 4 and 5 are side sectional views of the distal end of the biological agent delivery device of FIG. 2 depicting the delivery of a quantity of a biological agent to a tissue site.

Referring to FIGS. 1 and 2, biological agent delivery device 100 is an apparatus suitable for single-handed subcutaneous delivery of a biological agent 106 such as a quantity of a loose particulate drug, or a quantity of cells, cell clusters or cellular extracts in solution with a biological compatible carrier. For purposes of illustrating the invention, we have selected a delivery device similar to the device disclosed in U.S. Pat. No. 5,562,613 which is incorporated herein by reference in its entirety. However, other mechanisms for inserting and retracting the various members may substitute therefore. Additionally, for illustration purposes, the biological agent 106 depicted in the drawings is a particulate drug.

Delivery device 100 has a housing 12 with a pair of finger grips 14 extending transverse the longitudinal axis of the housing. A driving member 16 is slideably engaged with a track 20 formed along the longitudinal length of housing 12. The housing 12 has an external cylindrical bore 18 formed therein which extends along the longitudinal axis of the housing 12. A tubular member or cannula 104, having an internal bore 104*c* is mounted within the external cylindrical bore 18 and extends along the longitudinal axis of bore 18. A piston 108 is shown disposed within internal bore 104*c*. Cannula 104 has a solid distal tip 104*a* which is angled for penetration into tissue. A radially lateral opening in the cannula 104 near tip 104*a* forms a cannula notch 104*b* (FIG. 3). An outer tube 102 is secured to housing 12 and is mounted concentrically about cannula 104. Cannula 104 is axially slideable relative to cylindrical bore 18 and outer tube 102 for extending or retracting cannula 104 relative to outer tube 102 in order to enclose or expose cannula notch 104*c*. A flexible membrane 105 having a collapsible support surface 105*a*, a tubular portion 105*b* and a closed distal end 105*c* is positioned coaxially within bore 104*c* of cannula 104. The distal end 105*c* of membrane 105 extends into cannula notch 104*b* and abuts the distal end 103 of cannula notch 104*b*. Flexible membrane 105 extends across the opening of cannula notch 104*b* and prevents bore 104*c* from communicating with regions outside cannula 104 through cannula notch 104*b*. Piston 108 is mounted coaxially within the tubular portion 105*b* of the flexible membrane 105. Piston 108 is axially slideable relative to cannula 104 and tubular portion 105*b* and acts as a displacement member for radially, laterally displacing support surface 105*a*. Since the bore 104*c* within cannula 104 terminates at the distal end 103 of cannula notch 104*b*, piston 108 is restricted from extending past cannula notch 104*b*.

The support surface 105*a* of flexible membrane 105 is located near the distal end 105*c* of the membrane 105 for supporting a quantity of a biological agent 106. The support surface 105*a* is changeable from an undisplaced or collapsed position to a displaced position. When membrane 105 is an undisplaced position, support surface 105*a* is indented downwardly (or inwardly) into flexible membrane 105 to form a pouch with support surface 105*a* contacting the opposite side of the membrane 105. The pouch is typically formed by pushing support surface 105*a* downwardly (inwardly). The support surface 105*a* provides the surfaces of the pouch. Alternatively, the pouch can be preformed into membrane 105 such as by molding. When membrane 105 is in a displaced position, the pouch disappears with the support surface 105*a* being relatively horizontal. Membrane 105 is preferably formed from a flexible polymeric material which can either be stretchable or non-stretchable and can be transparent. Alternatively, membrane 105 can also be formed from other suitable flexible materials such as fabrics. Although tubular portion 105*b* is typically flexible, alternatively, tubular portion 105*b* can be rigid with only the support surface 105*a* being flexible.

The piston 108 and cannula 104 are secured at their respective proximal ends by a piston grip 48, and a cannula grip 50. The proximal end of tubular portion 105*b* of membrane 105 of has a flange 105*d* which secures tubular portion 105*b* to cannula 104 at the proximal end of cannula grip 50. Additionally, if needed, tubular portion 105*b* can be bonded within bore 104*c* with an adhesive. The piston grip 48 and cannula grip 50 are disc-shaped with a diameter which approximates the diameter of the cylindrical bore. The piston grip 48 and the cannula grip 50 are slideably engaged within the housing bore 18. The piston grip 48 and cannula grip 50 have respective channels formed therein through which drive pins 32 and 34 respectively extend for engagement with the proximal ends of the piston 108 and cannula 104 respectively.

Piston drive pin 32 and cannula drive pin 34 both extend through a single elongate slot 128 in housing 12. Housing slot 128 has a notch 128*a* located at its distal end for engaging cannula drive pin 34 when cannula drive pin 34 is in the advanced position. Piston drive pin 32 extends through driving member 16 through a hole 32*a*. Cannula drive pin 34 extends through driving member 16 through an elongate driving member slot 126. Driving member slot 126 has a notch 126*a* located at its distal end for engaging cannula drive pin 34.

The piston 108, cannula 104 and outer tube 102 are preferably formed of rigid sterilizable material such as stainless steel. Other components of the device, including the housing, driving member, piston and cannula grips, etc. are preferably made from low cost plastic material. The use of molded plastic components for the manufacture of the instrument is preferred to lower the cost so that the device can be disposed of after use.

In operation, in order to subcutaneously deliver a quantity of a biological agent 106 to a desired tissue site, the surface 112*a* of tissue 112 is first cut with a scalpel. The tip 104*a* of cannula 104 is then inserted into the incision within tissue 112 while driving member 16 is in a retracted position and the distal end 101 of delivery device 100 is advanced into tissue 112 until reaching a desired location. When driving member 16 is in a retracted position, cannula notch 104*b* is enclosed by outer tube 102 with the tip of piston 108 being at the proximal end of cannula notch 104*b*. Outer tube 102 protects the biological agent 106 and prevents it from spilling out of cannula notch 104*b* prematurely. Alternatively, tip 104*a* of cannula 104 can be inserted into tissue 112 by puncturing the surface 112*a* of tissue 112 with tip 104*a*.

Driving member 16 is then moved distally along track 20 toward the distal end 101 of delivery device 100. Cannula drive pin 34 is engaged within notch 126*a* of driving member slot 126 and piston drive pin 32 is engaged by hole 32*a*. As the driving member 16 is advanced, cannula 104 is extended from outer tube 102 such that cannula notch 104*b* and the biological agent 106 are exposed beyond the tip 102a of outer tube 102 as seen in FIG. 4. At the same time, driving member 16 advances piston 108 by engaging piston drive pin 32 with hole 32a such that the cannula 104 and the piston 108 advance together in unison. Cannula 104 is extended until cannula drive pin 34 reaches the distal end of housing slot 128 where cannula drive pin 34 engages housing slot notch 128a.

Figure 5:
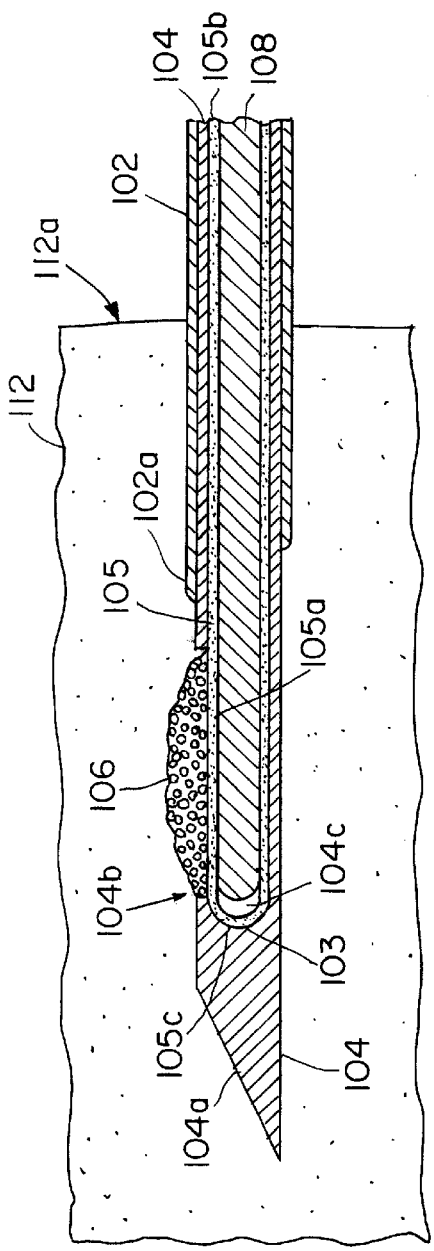

As driving member 16 is further advanced, cannula drive pin 34 disengages from notch 126a in driving member slot 126 and piston drive pin 32 is advanced further, thereby advancing piston 108 forward relative to cannula 104. As piston 108 is extended into cannula notch 104b, piston 108 laterally displaces the support surface 105a of membrane 105 thereby laterally displacing the biological agent 106 from cannula notch 104b into the surrounding tissue 112 as seen in FIG. 5. Piston 108 is extended into cannula notch 104b until the proximal end of driving member slot 126 reaches cannula drive pin 34, thereby preventing further advancement of driving member 16. Further advancement of piston 108 is also prevented by the distal end 103 of cannula notch 104b.

Once the biological agent 106 is deposited into tissue 112, the distal end 101 of delivery device 100 can be removed from tissue 112. To remove distal end 101 from the tissue 112, the cannula 104 and the piston 108 are first retracted relative to outer tube 102 by retracting driving member 16. This leaves behind the biological agent 106 within tissue 112. Distal end 101 of delivery device 100 is then pulled from tissue 112 leaving behind a small puncture wound.

Figure 6:
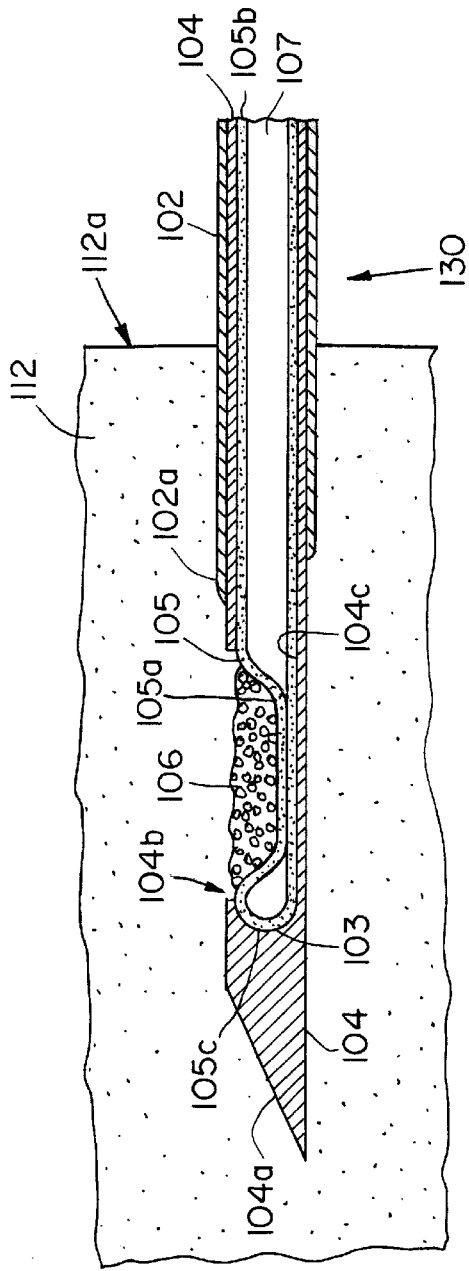
FIGS. 6 and 7 are side sectional views of the distal end of another preferred biological agent delivery device depicting the delivery of a quantity of a biological agent to a tissue site.
Figure 7:
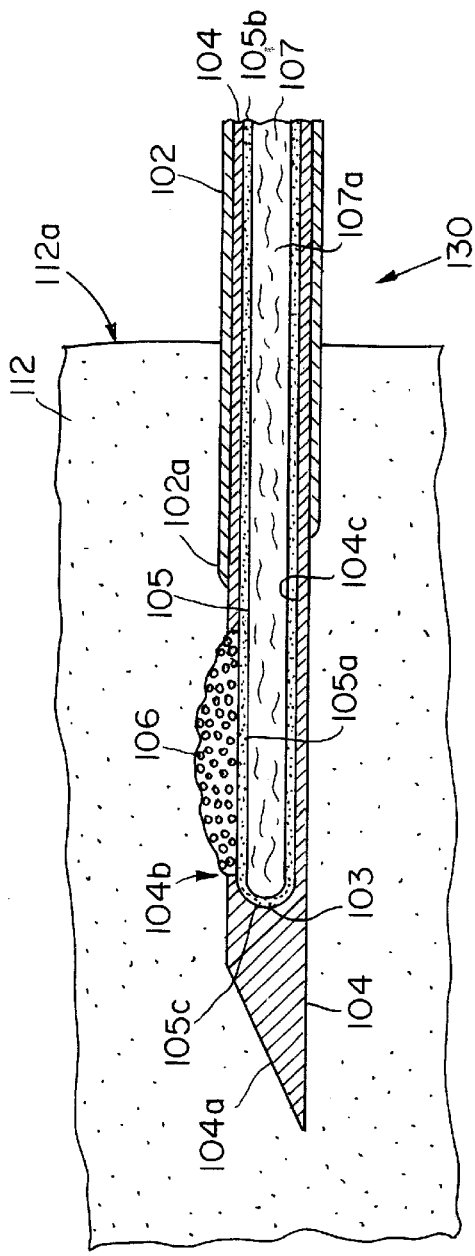
Figure 8:
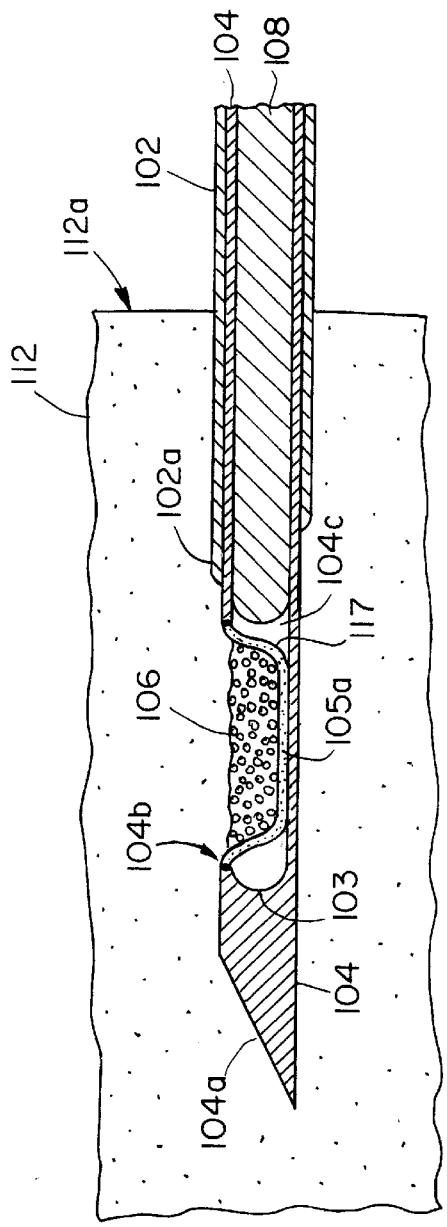
FIG. 8 is a side sectional view of the distal end of yet another preferred biological agent delivery device.
Figure 9:
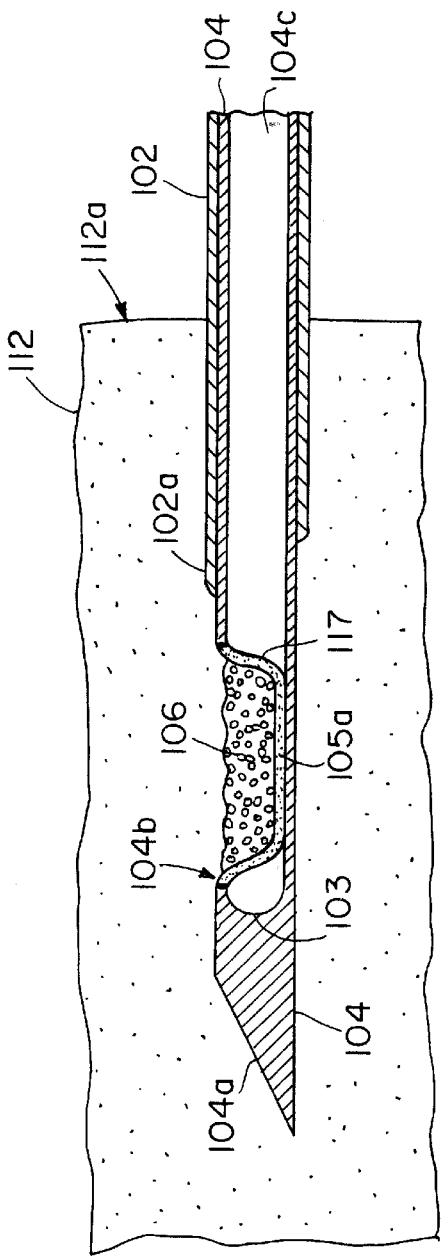
FIG. 9 is a side sectional view of the distal end of still another preferred biological agent delivery device.

FIGS. 6 and 7 depict the distal end of biological agent delivery device 130 which is another preferred embodiment of the present invention differing from delivery device 100 in that piston 108 and the components associated with advancing and retracting piston 108 are omitted. Instead, in order to deliver a biological agent 106, a fluid 107a such as a gas or a liquid is introduced into cavity 107 within membrane 105 to serve as a displacement member in order to laterally displace the support surface 105a. If desired, the fluid can outwardly displace support surface 105a past the outer surface of cannula 104 thereby forming an outward bulge in membrane 105. The fluid is preferably air if a gas is employed or saline solution if a liquid is employed and is preferably introduced into cavity 107 by a piston/plunger type mechanism or a closed loop pump mechanism within or attached to delivery device 130. Such a mechanism can be a syringe-type device or a calibrated ampoule-type device. Alternatively, the fluid can be introduced from a reservoir by a pump or from a pressurized tank and can be any other suitable gas or liquid.

Referring to FIGS. 8 and 9, flexible membrane 117 differs from flexible membrane 105 in that it does not include a tubular portion 105*b* but consists of a flexible membrane extending across and sealed over the lateral opening of cannula notch 104*b*. As a result, in the embodiment shown in FIG. 8, the piston 108 contacts and slides within bore 104*c* of cannula 104. In the embodiment depicted in FIG. 9, the support surface 105*a* of membrane 117 is laterally displaced by a fluid such as gas or liquid introduced into bore 104*c* of cannula 104.

Referring to FIG. 10, biological agent delivery device 132 is a flexible catheter for insertion into body cavities of a patient. In order to provide flexibility of the catheter, the cannula 104 and outer tube 102 are made of flexible material. As in delivery device 130, the support surface 105*a* of flexible membrane 105 is displaced by fluid introduced into cavity 107. Cannula 104 has a blunt tip 115 to facilitate the passage of delivery device 132 through body cavities. Although delivery device 132 is shown to include flexible membrane 105, alternatively, flexible membrane 117 may be employed instead.

An optional fiber optic bundle 109 including optical fibers 109*a*, 109*b* and 109*c* is positioned within bore 104*c* of cannula 104 alongside tubular portion 105*b* of membrane 105. Optical fiber 109*c* is directed laterally with respect to cannula 104 to provide light to a desired drug delivery site for optimized drug absorption. Illumination is also useful when delivering cells, subcellular extracts, plasmids or gene products for genetic therapy because it facilitates gene transfer. In addition, other forms of electromagnetic radiation can be delivered by optical fiber 109*c*, for example, ultra-violet light for altering cell membranes or for sterilization, or to increase cell membrane permeability with blue light. Furthermore, optics for viewing the delivery site are provided by laterally positioning optical fiber 109*b* and lens 111. Finally, optics for forward viewing are provided by optical fiber 109*a* and lens 113.

The fluids (liquids or gases) employed for displacing the support surface 105*a* in the embodiments depicted in FIGS. 6, 7, 9 and 10 can be temperature controlled over a range of different temperatures for therapeutic purposes. The temperature of the fluid is controlled by a cooling/heating system which is coupled to the fluid delivery system. For example, a cold fluid can be used for cooling the tissue surrounding the delivery site for constricting the capillaries in that tissue so that the delivered biological agent passes into the bloodstream more slowly. Alternatively, a heated fluid can be used for heating the tissue surrounding the delivery site for widening the capillaries so that the delivered biological agent passes into the bloodstream more rapidly. In this manner, the delivery rate of the biological agent can be controlled. In addition, extreme cold or hot fluids can be used to freeze or coagulate tissue, if desired.

Although the present invention biological agent delivery devices of FIGS. 1–10 have been described above for primarily delivering particulate or liquid biological agents, biological agents in pellet form can also be delivered. The term "biological agent" is meant to encompass any substance that can be introduced into tissue or a body cavity for treating a patient such as drugs, microspheres, cells, cell clusters, cells transfected with foreign DNA, cellular components, cellular extracts or gene products. The term "drug" as used herein is intended to have a broad construction so as to include any type of medication capable of being administered in the manner described herein. When biological agents in a liquid form are delivered, a sealing arrangement can be provided around cannula notch 104*b* to reduce the possibility that liquid will not leak prematurely from cannula notch 104*b* when outer tube 102 encloses cannula notch 104*b*.

Referring to FIGS. 11 and 12, biological agent delivery catheter 210 is another preferred biological agent delivery device for delivering biological agents 222. Catheter 210 includes an elongate tubular sheath 212 formed of flexible material. The distal end of sheath 212 terminates at a curved blunt tip 214. A guide wire 216 for guiding catheter 210 within a body cavity extends within the interior 226 of sheath 212 along the longitudinal axis of sheath 212 and is secured to tip 214. Two displaceable pouch systems 224a and 224b for containing and delivering biological agents 222 are positioned near the tip 214 of catheter 210.

The pouch systems 224a/224b are spaced apart from each other along the length of sheath 212 and each include an annular pouch or pocket 220 encircling the circumference of the sheath 212. The pouches 220 are preferably formed of a thinner, more flexible membrane 252 than sheath 212 and are bonded to the wall 213 of sheath 212. The pouches 220 are radially inwardly indented into the interior 226 of sheath 212 and can be preformed into this shape. Pouches 220 form recessed regions for containing or storing biological agents 222 away from the outer perimeter of sheath 212 and include a support surface 220a for supporting biological agents 222 therein. Opposing edges 215 of the wall 213 of sheath 212 are positioned adjacent to each other which causes the membranes of pouches 220 to form a substantially enclosed inward loop to so that the biological agents 222 do not prematurely spill from the pouches 220. This protects the biological agents 222 during insertion of the catheter 210 within a body cavity. The biological agents 222 are similar to the biological agents 106 previously described above. A spring member 218 is coupled to tip 214 between the guide wire 216 and the tip 214 for causing the delivery of the biological agents 222.

Figure 12:
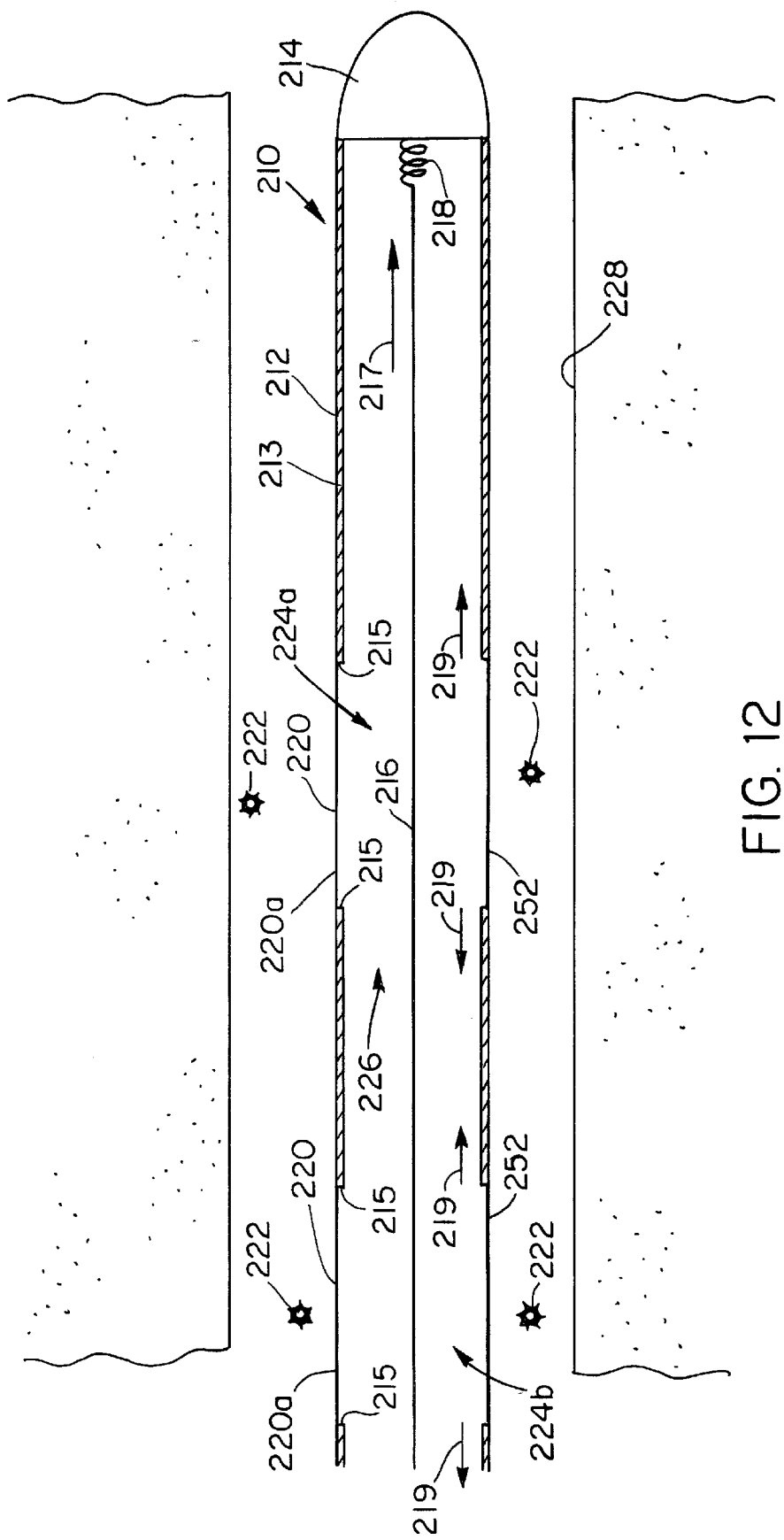
FIG. 12 is a side schematic view of the catheter of FIG. 11 positioned within a body passage with the pouches displaced laterally outward to release the biological agents.
Figure 16:
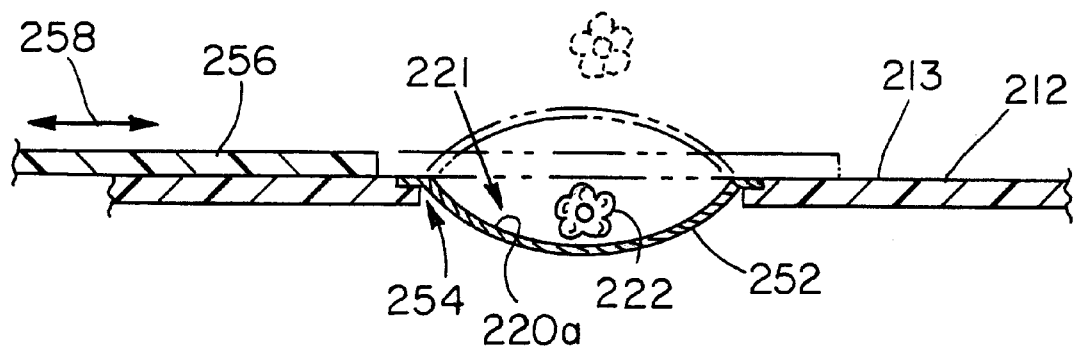
FIG. 16 is a side-sectional view of still another preferred pouch arrangement.
Figure 17:
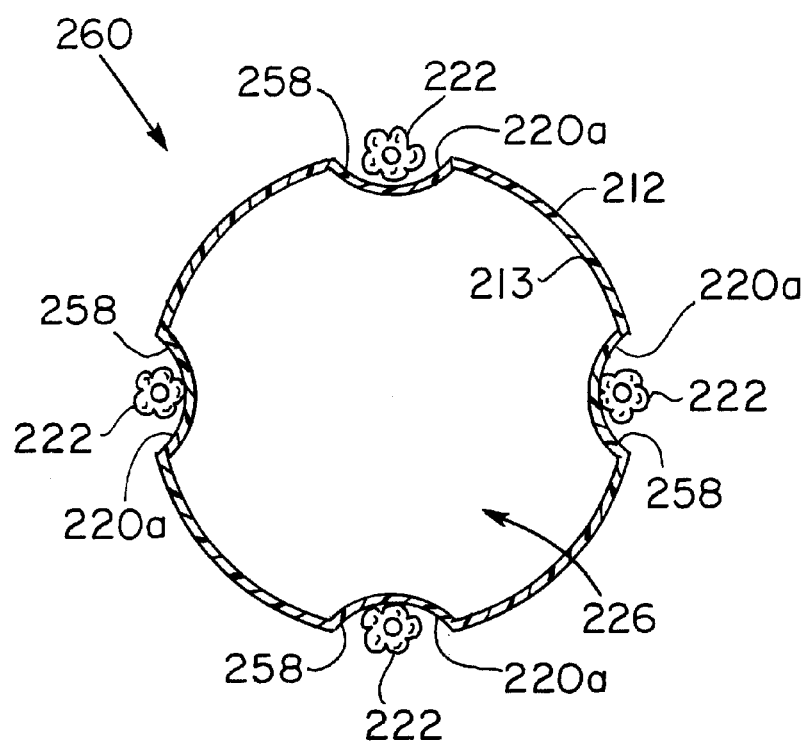
FIG. 17 is a cross-sectional view of yet another preferred pouch arrangement.

Referring to FIG. 12, in operation, catheter 210 is inserted within a body lumen or cavity 228. Catheter 210 is advanced within the cavity 228 while being guided by guide wire 216 until reaching a desired location for the delivery of the biological agents 222. Release of the spring member 218 causes stretching or lengthening of sheath 212 in the direction of arrow 217 which pulls edges 215 away from each other as shown by arrows 219 and displaces pouches 220 radially or laterally outward into a flattened state relative to the longitudinal axis of sheath 212. This causes the release of the biological agents 222 radially or laterally outward from catheter 210 relative to the longitudinal axis to the desired treatment location.

Although pouches 220 are preferably formed from a membrane 252 that is bonded to sheath 212, alternatively, pouches 220 can be integrally formed from the wall 213 of the sheath 212. In such a case, the pouches 220 would be formed to be more flexible than the surrounding wall 213.

Figure 10:
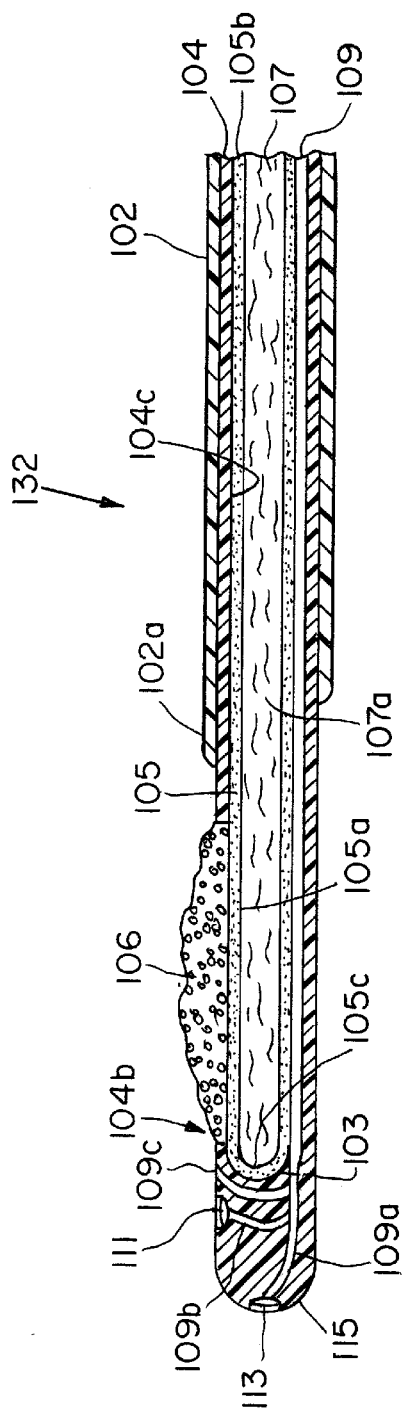
FIG. 10 is a side sectional view of the distal end of still another preferred biological agent delivery device.

Referring to FIG. 13, biological agent delivery catheter 230 is another preferred catheter. Catheter 230 differs from catheter 210 in that a fluid 232 is introduced into the interior 226 of sheath 212 for lengthening sheath 212 to radially or laterally outwardly displace the pouches 220 of pouch systems 224a/224b. Fluid 232 can be a liquid or a gas depending upon the application at hand. Also, depending upon the pressure of fluid 232, the outwardly displaced pouches 220 can be displaced flush with the wall 213 of sheath 212 or outwardly bulging as depicted in phantom. Tip 214 is formed of an optically transmissive material for transmitting light 234 received from a light source 233. The light 234 is transmitted through the interior 226 of sheath 212 by fluid 232. Tip 214 is preferably formed from a solid piece of material that is secured to sheath 212, but alternatively, can be hollow or integrally formed with sheath 212. The shape and design of tip 214 is made to produce a desired pattern of transmitted light. As a result, tip 214 can be of other suitable shapes depending upon the application at hand and can include mirrors if desired. Various types of light can be transmitted as previously discussed with respect to FIG. 10.

Referring to FIG. 14, biological agent delivery catheter 240 is another preferred catheter which differs from catheter 230 in that catheter 240 includes a balloon 246 for controlling the flow of fluids such as blood around catheter 240 when catheter 240 is introduced within a passage such as a vein or artery. A central tube 242 is positioned within the interior 226 of sheath 212, thereby forming an outer annular region 236 into which the fluid 232 is introduced for radially or laterally outwardly displacing the pouches 220. Tube 242 has an interior region 244 which is coupled in fluid communication with the interior 248 of balloon 246 via passages 250 so that balloon 246 can be inflated independently from the operation of pouch systems 224a/224b. Finally, a fiber optic 238 extends within the interior 244 of tube 242 for transmitting light to tip 214.

FIG. 15 depicts another preferred pouch system 235 which includes a shallow preformed indented annular pouch 236 within sheath 212. The edges 215 of the wall 213 of sheath 212 are positioned further apart from each other than with pouches 220. A rupturable membrane 237 having a weakened region 237*a* (for example, perforations) covers pouch 236 to prevent premature release of the biological agents 222.

Referring to FIG. 16, pouch 221 is another preferred pouch which differs from pouch 220 in that instead of being a single annular pouch encircling sheath 212, pouch 221 is only one of multiple pouches 221 encircling sheath 212. Membrane 252 is bonded to the edges of a circular or oval opening 254 within sheath 212. Membrane 252 can be preformed to extend inwardly into the interior 226 of sheath 212. The biological agent 222 is released when the membrane 252 is displaced outwardly as shown in phantom. A flexible outer sleeve 256 is included which extends around sheath 212. Sleeve 256 is longitudinally slidable relative to sheath 212 as shown by arrows 258 to cover pouch 221 (shown in phantom) during insertion into a patient to prevent premature release of biological agent 222. Sleeve 256 is slidably retracted relative to pouch 221 to allow biological agent 222 to be delivered.

FIG. 17 is another preferred pouch system 260 in which the pouches 258 differ from pouch 221 (FIG. 16) in that pouches 258 are integrally formed from the wall 213 of sheath 212. The sheath can be hardened in the areas surrounding the pouches 258 so that the pouches 258 remain flexible. In order to prevent premature release of the biological agents 222, the rupturable membrane 237 (FIG. 15) or the slidable outer sleeve 256 (FIG. 16) can be employed. Although four pouches 258 are depicted to encircle the circumference of sheath 212, alternatively more than four or less than four can be employed. The number of pouches 258 can be determined by the diameter of sheath 212.

While this invention has been particularly shown and described with references to preferred embodiments thereof, it will be understood by those skilled in the art that various changes in form and details may be made therein without departing from the spirit and scope of the invention as defined by the appended claims. For example, other mechanisms can be employed for advancing and retracting cannula 104 and piston 108. Such mechanisms can include motor or hand-operated gears and power screws, or fluid operated cylinders. In addition, the present invention delivery devices and catheters can be employed for implanting non-therapeutic, solid or rigid objects into tissue or body cavities such as tracking devices, radio transmitters or pumps. Furthermore, various features of the above discussed delivery devices and catheters can be combined or omitted.

What is claimed is:

1. A biological agent delivery device comprising:
   a sheath having a longitudinally extending wall surrounding an interior region, and a closed tip at a distal end; and
   a flexible circumferential pouch system formed in the sheath wall and encircling the sheath including at least one annular pouch, the pouch system having a closed position and a open position, the closed position for containing a biological agent in a circular manner about the sheath and the open position for displacing the biological agent outwardly in a circular manner.

2. The delivery device of claim 1 further comprising a displacement member disposed within the sheath for causing displacement of the pouch system radially with respect to the sheath to deliver the biological agent.

3. The delivery device of claim 2 in which the displacement member comprises a spring member for elongating the sheath.

4. The delivery device of claim 1 in which the displacement member comprises a volume of fluid.

5. The delivery device of claim 4 in which the fluid is a liquid.

6. The delivery device of claim 5 in which the fluid is a gas.

7. The delivery device of claim 4 further comprising a light source for directing light within the sheath, the fluid capable of transmitting the light to the tip.

8. The delivery device of claim 7 in which the tip is formed to produce a desired pattern of light.

9. The delivery device of claim 1 further comprising:
   a light source for directing light within the sheath; and
   a fiber optic disposed within the sheath for transmitting the light to the tip.

10. The delivery device of claim 1 further comprising a balloon extending from the sheath for controlling fluid flow within body cavities.

11. The delivery device of claim 1 in which the pouch system is preformed.

12. The delivery device of claim 11 in which the sheath is flexible and the pouch system is preformed in the sheath wall.

13. The delivery device of claim 12 further comprising a guide wire extending within the sheath for guiding the delivery device.

14. A biological agent delivery catheter comprising:
    a flexible sheath having a longitudinally extending wall surrounding an interior region, and a closed tip at a distal end;
    a radially facing flexible circumferential pouch system formed in the sheath wall and encircling the sheath including at least one annular pouch, the pouch system having a closed position and a open position, the closed position for containing a biological agent in a circular manner about the sheath and the open position for displacing the biological agent outwardly in a circular manner;
    a guide wire extending within the sheath for guiding the catheter; and
    a displacement member disposed within the sheath for causing the pouch to be displaced to the open position to deliver the biological agent outwardly in a circular manner.

15. A method of forming a biological agent delivery device comprising the steps of:
    providing a sheath having a longitudinally extending wall surrounding an interior region, and a closed tip at a distal end;
    providing the sheath with a flexible circumferential pouch system including at least one annular pouch for containing a biological agent formed in the sheath wall in a circular manner capable of being displaced radially outwardly circumferentially for radially displacing the biological agent.

16. The method of claim 15 further comprising the step of disposing a displacement member within the sheath for displacing the pouch system radially with respect to the sheath to deliver the biological agent.

17. The method of claim 16 further comprising the step of forming the displacement member from a spring member.

18. The method of claim 15 further comprising the step of forming the displacement member from a volume of fluid.

19. The method of claim 18 further comprising the steps of providing a light source for directing light within the sheath, the fluid capable of transmitting the light to the tip with the fluid.

20. The method of claim 19 further comprising the step of forming the tip to produce a desired pattern of light.

21. The method of claim 15 further comprising the steps of:
    providing a light source for directing light within the sheath; and
    disposing a fiber optic within the sheath for transmitting the light to the tip.

22. The method of claim 15 further comprising the step of providing a balloon capable of extending from the sheath for controlling fluid flow within body cavities.

23. The method of claim 15 further comprising the step of preforming the pouch system.

24. The method of claim 23 further comprising the steps of:
    forming the sheath from flexible material; and
    preforming the pouch system in the sheath wall.

25. The method of claim 24 further comprising the step of extending a guide wire within the sheath for guiding the delivery device.

26. A method of delivering a biological agent to a tissue site comprising the steps of:
    providing a sheath having a longitudinally extending wall surrounding an interior region, and a closed tip at a distal end;
    containing a biological agent within a flexible circumferential pouch system formed in the sheath wall encircling the sheath including at least one annular pouch, the pouch system having a closed position and a open position, the closed position for containing a biological agent in a circular manner about the sheath and the open position for displacing the biological agent outwardly in a circular manner;

inserting the sheath into the tissue site; and radially displacing the pouch outwardly to the open position with a displacement member disposed within the sheath to deliver the biological agent outwardly in a circular manner to the tissue site.

27. A biological agent delivery device comprising:

a sheath having a longitudinally extending wall surrounding an interior region, and a closed tip at a distal end;

a flexible pouch formed in the sheath wall for containing a biological agent capable of being displaced radially outwardly for radially displacing the biological agent; and a displacement member comprising a spring member disposed within the sheath for elongating the sheath and causing displacement of the pouch radially with respect to the sheath to deliver the biological agent.

28. A method of forming a biological agent delivery device comprising the steps of:

providing a sheath having a longitudinally extending wall surrounding an interior region, and a closed tip at a distal end;

providing the sheath with a flexible pouch for containing a biological agent formed in the sheath wall capable of being displaced radially outwardly for radially displacing the biological agent; and disposing a displacement member formed from a spring member within the sheath for displacing the pouch radially with respect to the sheath to deliver the biological agent.

29. A biological agent delivery device comprising:

a sheath having a longitudinally extending wall surrounding an interior region, and a closed tip at a distal end; and flexible annular pouch formed in the sheath wall and encircling the sheath for containing a biological agent and capable of being displaced radially outwardly for radially displacing the biological agent.

30. A method of delivering a biological agent to a tissue site comprising the steps of:

providing a sheath having a longitudinally extending wall surrounding an interior region, and a closed tip at a distal end;

containing a biological agent within a flexible annular pouch formed in the sheath wall and encircling the sheath;

inserting the sheath into the tissue site; and radially displacing the pouch outwardly with a displacement member disposed within the sheath to deliver the biological agent to the tissue site.

\* \* \* \* \*